United States Patent [19]
Oxenius et al.

[11] Patent Number: 4,855,410
[45] Date of Patent: Aug. 8, 1989

[54] PROCESS FOR THE PREPARATION OF FIBRE-REACTIVE AZO COMPOUNDS CONTAINING A PHENYLENEDIAMINE DIAZO COMPONENT

[75] Inventors: Rüdiger Oxenius, Rheinfelden, Fed. Rep. of Germany; Charles Wilhelm, Leymen, France

[73] Assignee: Ciba-Geigy Corporation, Ardsley, N.Y.

[21] Appl. No.: 883,891

[22] Filed: Jul. 9, 1986

[30] Foreign Application Priority Data

Jul. 30, 1985 [CH] Switzerland ............ 3305/85

[51] Int. Cl.$^4$ ............ C09B 62/026; C09B 62/66; C09B 62/665
[52] U.S. Cl. ............ 534/591; 534/598; 534/643; 534/636; 534/634; 534/638
[58] Field of Search ............ 534/643, 595, 598, 638, 534/636

[56] References Cited

U.S. PATENT DOCUMENTS

| | | | |
|---|---|---|---|
| 2,910,464 | 10/1959 | Fasciati et al. | 534/578 X |
| 3,027,362 | 3/1962 | Galb et al. | 534/638 X |
| 3,223,470 | 12/1965 | Boedeker et al. | 534/638 X |
| 3,225,027 | 12/1965 | Baker et al. | 534/643 |
| 3,488,343 | 1/1970 | de Montmollin et al. | 534/643 |
| 3,558,592 | 1/1971 | de Montmollin et al. | 534/643 |
| 3,642,765 | 2/1972 | Oesterlein et al. | 534/638 |
| 3,755,290 | 8/1973 | de Montmollin et al. | 534/643 |
| 3,910,758 | 11/1975 | Bien et al. | 534/638 |
| 4,210,582 | 7/1980 | de Montmollin et al. | 534/643 |
| 4,740,597 | 4/1988 | Franke et al. | 544/204 |

FOREIGN PATENT DOCUMENTS

| | | | |
|---|---|---|---|
| 1112225 | 8/1961 | Fed. Rep. of Germany | 534/578 |
| 2145391 | 3/1972 | Fed. Rep. of Germany | 534/643 |
| 2818654 | 12/1978 | Fed. Rep. of Germany | 534/638 |
| 536353 | 6/1973 | Switzerland | 534/643 |
| 1166913 | 10/1969 | United Kingdom | 534/643 |

OTHER PUBLICATIONS

Venkataraman, The Chemistry of Synthetic Dyes, vol. VI, Reactive Dyes (1972) pp. 211–217.
Beech, "Fibre-Reactive Dyes", Logo Press Limited, London, p. 98, (1970).

*Primary Examiner*—Floyd D. Higel
*Attorney, Agent, or Firm*—Kevin T. Mansfield; Edward McC. Roberts

[57] ABSTRACT

The invention relates to a process for the preparation of azo compounds of the formula

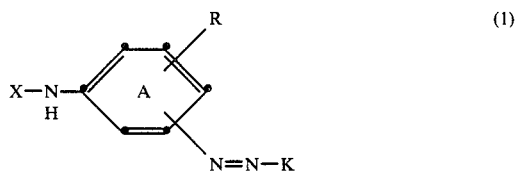

(1)

wherein K is the radical of a coupling component, R is a water-solubilising group and X is a fibre-reactive radical, and the benzene ring A may be further substituted, which process comprises reacting a compound of the formula

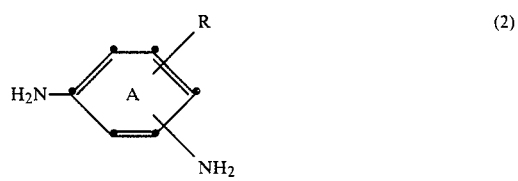

(2)

in an aqueous medium containing 5 to 25% by weight of an alkali metal halide or alkali metal sulfate, based on the weight of the medium, with a compound which introduces the radical X to give the compound of the formula

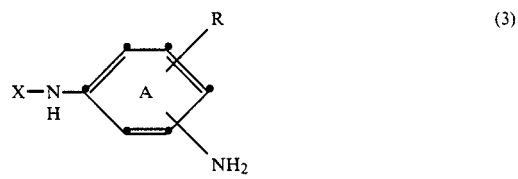

(3)

diazotising said compound direct and coupling the diazotisation product with a coupling component of the formula

H—K    (4)

in which formulae (2), (3) and (4) A, R, X and K are as defined for formula (1).

16 Claims, No Drawings

PROCESS FOR THE PREPARATION OF FIBRE-REACTIVE AZO COMPOUNDS CONTAINING A PHENYLENEDIAMINE DIAZO COMPONENT

The present invention relates to a novel process for the preparation of water-soluble, fibre-reactive azo compounds containing a phenylenediamine diazo component, the one free amino group of which is acylated in the presence of salts, so that said amino group becomes fibre-reactive.

The hitherto known conventional processes for the preparation of azo compounds containing a fibre-reactive N-acylated phenylenediamine diazo component comprise e.g.:

(a) condensing a phenylenediamine with a compound introduces the reactive radical, purifying the resultant intermediate and effecting subsequent diazotisation and coupling; or (b) condensing a phenylenediamine with a protecting group, e.g. acetyl chloride, purifying the resultant intermediate, effecting subsequent diazotisation and coupling, then removing the protecting group and condensing the free amino group with a compound which introduces the reactive radical.

A drawback of both process variants is the necessary separation of the N-monoacylated phenylenediamine from the starting materials and from the N,N-diacylated phenylenediamine.

A further drawback of the second process variant is that coupling components which contain free amino groups may also be able to react with the fibre-reactive acylating agent.

Surprisingly, a novel process has been found which does not have these drawbacks and which makes it possible to prepare in simple manner water-soluble azo compounds containing a fibre-reactive N-acylated phenylenediamine diazo component without purification or isolation of the intermediates.

Accordingly, the present invention relates to a process for the preparation of azo compounds of the formula

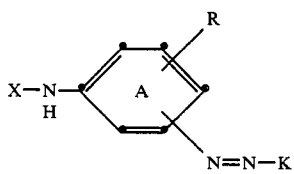

wherein K is the radical of a coupling component, R is a water-solubilising group and X is a fibre-reactive radical, and the benzene ring A may be further substituted, which process comprises reacting a compound of the formula

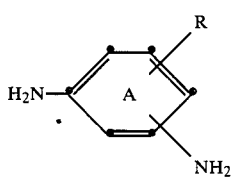

in an aqueous medium containing 5 to 25% by weight of an alkali metal halide or alkali metal sulfate, based on the weight of the medium, with a compound which introduces the radical X to give the compound of the formula

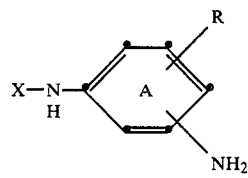

diazotising said compound direct and coupling the diazotisation product with a coupling component of the formula $$H-K \qquad (4)$$

in which formulae (2), (3) and (4) A, R, X and K are as defined for formula (1). A preferred embodiment of the process of this invention is characterised in that the benzene ring A in formula (1) is not further substituted.

Surprisingly, when following this procedure, the complicated purification of the compound of formula (3) can be dispensed with, the reaction time of each process step can be shortened markedly and the azo compounds of formula (1) can be obtained in greater purity than by the hitherto known conventional processes. Furthermore, by following the procedure of this invention, the yield is increased considerably.

The phenylenediamines of formula (2) eligible for use in the process of this invention are preferably 1,3-phenylenediamines and, most preferably, 1,4-phenylenediamines which contain a water-solubilising group and which may be further substituted e.g. by $C_1$–$C_4$alkyl such as methyl, $C_1$–$C_4$alkoxy such as methoxy, or halogen such as fluorine, chlorine or bromine. Representative examples are: 1,3-phenylenediamine-4-sulfonic acid, 6-methoxy-1,3-phenylenediamine-4-sulfonic acid, 2-methylphenylsulfonyl-1,4-phenylenediamine, 2-ureido-1,4-phenylenediamine, 1,4-phenylenediamine-2-sulfonic acid and 2,5-diamino-4'-methyl-1,1'-diphenylsulfone-3'-sulfonic acid.

A suitable water-solubilising group R in formula (2) is one of the following groups: a sulfone group, a sulfonamide group, an N-monoalkylsulfonamide group, an N,N-dialkylsulfonamide group, a carboxyl group or a ureido group and, preferably, a sulfonic acid group.

A suitable sulfone group is an alkylsulfone group, preferably a $C_1$–$C_4$alkylsulfone group, or an arylsulfone group, preferably a phenylsulfone group, the phenyl ring of which may be further substituted, e.g. by $C_1$–$C_4$alkyl such as methyl, $C_1$–$C_4$alkoxy such as methoxy, halogen such as fluorine, chlorine or bromine, or sulfo.

A suitable N-monoalkylsulfonamide or N,N-dialkylsulfonamide group is in particular one containing one or two $C_1$–$C_4$alkyl groups.

In accordance with the process of the present invention, the acylation of the phenylenediamine of formula (2) with a compound which introduces the radical X is carried out in the presence of one of the salts indicated. The process of this invention is preferably carried out in the presence of further additional salts. Suitable salts are in particular mixtures of an alkali metal halide or an alkali metal sulfate and a salt which is preferably an acid acceptor, e.g. an alkali metal acetate, alkali metal hydroxide, alkali metal carbonate or alkali metal bicarbonate, or mixtures thereof.

Examples of suitable alkali metal halides are lithium fluoride, sodium fluoride, potassium fluoride, lithium chloride, sodium chloride, potassium chloride, lithium bromide, sodium bromide, potassium bromide, lithium iodide, sodium iodide or potassium iodide.

Examples of suitable alkali metal sulfates are sodium sulfate or potassium sulfate.

Examples of suitable acid acceptor salts are sodium acetate, sodium hydroxide, potassium hyxdroxide, sodium carbonate, potassium carbonate, sodium bicarbonate or potassium bicarbonate. It is preferred to use a mixture of sodium acetate and sodium bicarbonate in the process of this invention.

The amounts in which the acid acceptor salts are employed in the process of this invention may vary within wide limits and generally depend on the amount of acylating agent employed or on the amount of acid evolved during acylation. An excess of acid acceptor salts has generally proven advantageous.

The amount of alkali metal halide or alkali metal sulfate employed in the process of this invention depends on the volume or weight of the aqueous medium of the phenylenediamine of formula (2), i.e. the amount of alkali metal halide or alkali metal sulfate is independent on the amount of phenylenediamine dissolved beforehand. In general, 5 to 25% by weight of an alkali metal halide or alkali metal sulfate, based on the weight of the aqueous medium, have proven advantageous. In the process of this invention, it is preferred to employ 8 to 13% by weight of an alkali metal halide of alkali metal sulfate.

Suitable acylating agents which, in addition to containing the acylating site, also contain a preferably aliphatic, aromatic or heterocyclic reactive radical X are in particular the halides or anhydrides of organic acids which contain easily replaceable atoms or groups of atoms, and also heterocyclic compounds which contain easily replaceable atoms or groups of atoms.

No further working up of the reaction mass or suspension containing the product of formula (3) is required subsequent to the acylation of the compound of formula (2). The product of formula (3) can be diazotised immediately and the diazotisation product then coupled with a coupling component of formula (4). The diazotisation of the compound of formula (3) is effected by methods known per se, e.g. by treatment with nitrous acid in an aqueous solution of mineral acid at low temperature; the coupling with the coupling component of formula (4) is effected at acid, neutral or alkaline pH values.

Suitable coupling components of formula (4) are in particular those of the benzene, naphthalene or heterocyclic series.

Immediately after the coupling reaction, the azo compound of formula (1) is isolated in a manner known per se, e.g. by salting out, filtration and subsequent drying.

A conversion reaction which can sometimes be carried out immediately after the synthesis comprises, for example, treating a reactive dye of formula (1) which contains e.g. an $\alpha,\beta$-dibromopropionylamino radical with a dehydrohalogenating agent such as sodium hydroxide, so that the $\alpha,\beta$-dibromopropionylamino group is converted into the $\alpha$-bromoacryloyl group.

Preferred embodiments of the process of this invention are characterised in that (a) the weight ratio of water to the compound of formula (2) is in the range from 3:1 to 20:1, preferably from 4:1 to 8:1;

(b) 8 to 13% by weight of an alkali metal halide or alkali metal sulfate, preferably sodium chloride, are used;

(c) a buffered mixture of salts is used, preferably a mixture of an alkali metal carbonate, e.g. $Na_2CO_3$ or $K_2CO_3$, or an alkali metal bicarbonate, e.g. $NaHCO_3$ or $KHCO_3$, and an alkali metal acetate, e.g. sodium acetate or potassium acetate, and an alkali metal halide or alkali metal sulfate;

(d) the reaction of a compound of formula (2) with a compound which introduces the radical X is carried out in the temperature range from 0° to 20° C. and in the pH range from 3 to 9;

(e) the diazotisation is effected adiabatically at a temperature in the range from 0° to 70° C., in particular from 0° to 50° C., preferably from 20° to 50° C., most preferably from 20° to 40° C.;

(f) the coupling is effected adiabatically.

Further preferred embodiments of the process of this invention are characterised in that (g) a compound of formula (2) is used wherein R is a sulfophenylsulfone group or, preferably, a sulfonic acid group; it is most preferred to use as compound of formula (2) a 1,3-phenylenediaminesulfonic acid, in particular 1,3-phenylenediamine-4-sulfonic acid and, especially 1,4-phenylenediamine-2-sulfonic acid; a further interesting compound of formula (2) is 2,5-diamino-4'-methyl-1,1'-diphenylsulfone-3'-sulfonic acid;

(h) the compound which introduces the radical X is $\alpha,\beta$-dibromopropionyl chloride, $\alpha,\beta$-dichloropropionyl chloride or $\alpha$-chloroacryloyl chloride; further interesting compounds are bromoacetic anhydride and, in particular, chloroacetic anhydride or chloroacetyl chloride;

(i) the coupling component of formula (4) is a coupling component of the benzene, naphthalene or heteroacyclic series.

K is in particular the radical of an aminobenzene, alkoxybenzene, aminonaphthalene, alkoxynaphthalene, naphthol, aminonaphthol, pyrazolone, aminopyrazole, pyridone, pyrimidine, indole, naphthylimidazole, diphenylamine, pyrazolo[2,3-a]pyrimidine, tetrahydroquinoline or acetacetamide, which radicals may be further substituted by conventional substituents of azo dyes: e.g. $C_1$-$C_4$alkyl groups such as methyl, ethyl, propyl, isopropyl, butyl, isobutyl, sec-butyl and tert-butyl, $C_1$-$C_4$alkoxy groups such as methoxy, ethoxy, propyloxy, isopropyloxy, butyloxy, isobutyloxy, sec-butyloxy and tert-butyloxy, phenoxy, $C_1$-$C_6$alkanoylamino groups such as acetylamino or propionylamino, benzoylamino, amino groups such as $-NH_2$, methylamino, ethylamino, dimethylamino, diethylamino, cyanoethylamino, hydroxyethylamino, dihydroxyethylamino, cyclohexylamino, benzylamino and phenylamino, carboxylic acid ester groups such as methoxycarbonyl and ethoxycarbonyl, trifluoromethyl, nitro, cyano, acetyl, methylsulfonyl, carbamoyl, sulfamoyl, ureido, hydroxy, carboxy, sulfo, sulfomethyl and halogen such as fluorine, chlorine and bromine, as well as fibre-reactive radicals.

Preferred examples of coupling components of formula (4) are: 2-amino-8-naphthol-6-sulfonic acid, 2-methylamino-8-naphthol-6-sulfonic acid, 1-(2',5'-dichloro-4-sulfophenyl)-3-methylpyrazol-5-one, 1-(2'-chloro-6'-methylphenyl)-3-methylpyrazol-5-one, 1-hydroxy-3-sulfo-6-N-methyldibromopropionylaminonaphthalene, 2-aminonaphthalene-6-sulfonic acid, 1-(3'- or 4'-dibromopropionylaminobenzoylamino)-8-hydroxynaphthalene-4,6- or -3,6-disulfonic acid, 2-α-bromoacryloylamino-8-hydroxynaphthalene-6-sulfonic acid, 1-acetylamino-8-hydroxynaphthalene-4,6-disulfonic acid and 2-amino-8-hydroxynaphthalene-6-N-methyl-N-phenylsulfonamide.

It is most preferred to use an aminonaphthol sulfonic acid.

A particularly preferred embodiment of the process of this invention for the preparation of the azo dye of the formula

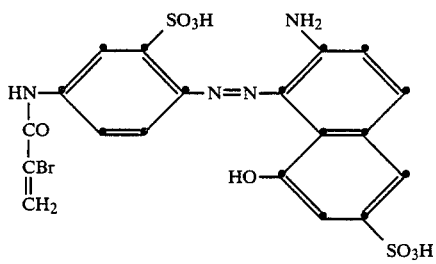
(5)

comprises reacting 1,4-phenylenediamine-2-sulfonic acid with α,β-dibromopropionyl chloride, diazotising the resultant compound direct without isolation, coupling the diazotisation product with 2-amino-8-hydroxynaphthalene-6-sulfonic acid and subsequently reacting the coupling product with a dehydrobrominating agent.

Another particularly preferred embodiment of the process of this invention for the preparation of the azo compound of the formula

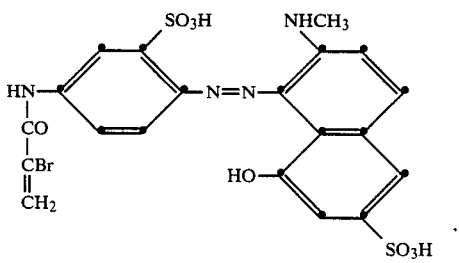
(6)

comprises reacting 1,4-phenylenediamine-2-sulfonic acid with α,β-dibromopropionyl chloride, diazotising the resultant compound direct without isolation, coupling the diazotisation product with 2-N-methylamino-7-hydroxynaphthalene-6-sulfonic acid and subsequently reacting the coupling product with a dehydrobrominating agent.

The analogous reaction of 1,3-phenylenediamine-4-sulfonic acid with chloroacetic anhydride or chloroacetyl chloride, with subsequent diazotisation and coupling in the 1-position with 2-amino-8-hydroxynaphthalene-6-sulfonic acid N-methyl-N-phenylamide, is also interesting.

Yet another particularly preferred embodiment of the process of this invention for the preparation of the azo dye of the formula

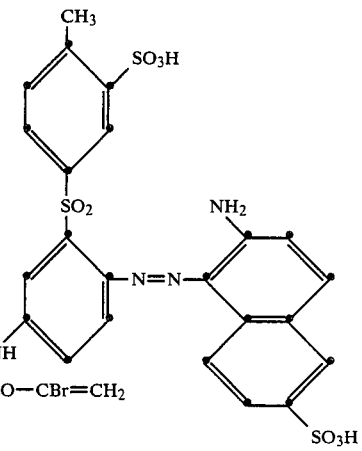

comprises reacting 2,5-diamino-4′-methyl-1,1′-diphenylsulfone-3′-sulfonic acid with α,β-dibromopropionyl chloride, diazotising the resultant compound direct without isolation or purification, coupling the diazotisation product with 2-aminonaphthalene-6-sulfonic acid and subsequently reacting the coupling product with a dehydrobrominating agent.

The starting materials of formulae (2) and (4) and the fibre-reactive acylating agents employed in the process of this invention are known per se and are prepared by known methods.

The sulfo group-containing azo compounds which can be prepared by the process of this invention are obtained either in the form of their free acid or, preferably, as salts thereof.

Examples of suitable salts are the alkali metal, alkaline earth metal or ammonium salts or the salts of an organic amine. Representative examples are the sodium, lithium, potassium or ammonium salts or the salt of triethanolamine.

Examples of acylating agents eligible for use in the process of the present invention are: bromo- or chloroacetic anhydride, chloro- or bromoacetyl chloride, β-chloro- or β-bromopropionyl chloride, α,β-dichloro- or α,β-dibromopropionyl chloride, chloromaleic anhydride, carbyl sulfate, acryloyl chloride, β-chloro- or β-bromoacryloyl chloride, α-chloroacryloyl chloride, α,β-dichloro- or α,β-dibromoacryloyl chloride, trichloroacryloyl chloride, chlorocrotonyl chloride, propiolyl chloride, 3,5-dinitro-4-chlorobenzenesulfochloride or 3,5-dinitro-4-chlorobenzenecarboxylic acid chloride, 3-nitro-4-chlorobenzenesulfochloride or 3-nitro-4-chlorobenzenecarboxylic acid chloride, 2,2,3,3-tetrafluorocyclobutane-1-carboxylic acid chloride, 2,2,3,3-tetrafluorocyclobutylacryloyl chloride, β-chloroethylsulfonyl-endomethylene-cyclohexanecarboxylic acid chloride, acrylsulfonyl-endomethylene-cyclohexanecarboxylic acid chloride, 2-chlorobenzoxazolecarboxylic acid chloride, 2-chlorobenzthiazolecarboxylic acid chloride, 2-chlorobenzthiazolesulfochloride, 4,5-dichloro-1-phenylpyridazonecarboxylic acid chloride or 4,5-dichloro-1-phenylpyridazonesulfochloride, 4,5-dichloropyridazolpropionyl chloride, 1,4-dichlorophthalazinecarboxylic acid chloride or 1,4-dichlorophthalazinesulfochloride, 2,3-dichloroquinoxalinecarboxylic acid chloride or 2,3-dichloroquinoxalinesulfochloride, 2,4-dichloroquinazolinecarboxylic acid chloride or 2,4-dichloroquinazolinesulfochloride, 2-methanesulfonyl-4-chloro-6-methylpyrimidine, 2,4-bismethanesulfonyl-6-methylpyrimidine, 2,4,6-tri- or 2,4,5,6-tetrachloropyrimidine, 2,4,6-tri- or 2,4,5,6-tetrabromopyrimidine, 2-methanesulfonyl-4,5-dichloro-6-methylpyrimidine, 2,4-dichloropyrimidine-5-sulfonic acid, 5-nitro- or 5-cyano-2,4,6-trichloropyrimidine, 2,6-bismethanesulfonylpyridine-4-carboxylic acid chloride, 2,4-dichloro-5-chloromethyl-6-methylpyrimidine, 2,4-dibromo-5-bromomethyl-6-methylpyrimidine, 2,4-dichloro-5-chloromethylpyrimidine, 2,4-dibromo-5-bromomethylpyrimidine, 2,5,6-trichloro-4-methylpyrimidine, 2,6-dichloro-5-trichloromethylpyrimidine, 2,4-bismethylsulfonyl-5-chloro-6-methylpyrimidine, 2,4,6-trimethylsulfonyl-1,3,5-triazine, 2,4-dichloropyrimidine, 3,6-dichloropyridazine, 3,6-dichloropyridazine-5-carboxylic acid chloride, 2,6-dichloro- or 2,6-dibromo-4-carboethoxypyrimidine, 2,4,5-trichloropyrimidine, 2,4-dichloropyrimidine-6-carboxylic acid chloride, 2,4-dichloropyrimidine-5-carboxylic acid chloride, 2,6-dichloro- or 2,6-dibromopyrimidine-4- or -5-carboxamide or -sulfonamide or -4- or -5-sulfochloride, 2,4,5,6-tetrachloropyridazine, 5-bromo-2,4,6-trichloropyrimidine, 5-acetyl-2,4,6-trichloropyrimidine, 5-nitro-6-methyl-2,4-dichloropyrimidine, 2-chlorobenzthiazole-6-carboxylic acid chloride, 2-chlorobenzthiazole-6-sulfochloride, 5-nitro-6-methyl-2,4-dichloropyrimidine, 2,4,6-trichloro-5-bromopyrimidine, 2,4,5,6-tetrafluoropyrimidine, 4,6-difluoro-5-chloropyrimidine, 2,4,6-trifluoro-5-chloropyrimidine, 2,4,5-trifluoropyrimidine, 2,4,6-trichloro(-tribromo- or -trifluoro)-s-triazine, and also 4,6-dichloro(-dibromo- or -difluoro)-s-triazines which are substituted in the 2-position by an aryl or alkyl radical, for example a phenyl, methyl or ethyl radical, or by the radical of an aliphatic or aromatic mercapto compound which is bonded through the sulfur atom or by the radical of an aliphatic or aromatic hydroxy compound which is bonded through the oxygen atom, or in particular by an —NH$_2$ group or by the radical of an aliphatic, heterocyclic or aromatic amino compound which is bonded through the nitrogen atom.

The 4,6-dihalo-s-triazines which are substituted in the 2-position are obtained, for example, by reaction of trihalo-s-triazines with the above amino, hydroxyl or mercapto compounds. The substituent in the 2-position of a 4,6-dihalo-s-triazine can be for example the radical of one of the following amino, hydroxy and mercapto compounds: ammonia, methylamine, dimethylamine, ethylamine, diethylamine, propylamine, isopropylamine, butylamine, dibutylamine, isobutylamine, sec-butylamine, tert-butylamine, hexylamine, methoxyethylamine, ethoxyethylamine, methoxypropylamine, chloroethylamine, hydroxyethylamine, dihydroxyethylamine, hydroxypropylamine, aminoethanesulfonic acid, β-sulfatoethylamine, benzylamine, cyclohexylamine, aniline, o-, m- and p-toluidine, 2,3-, 2,4-, 2,5-, 2,6-, 3,4- and 3,5-dimethylaniline, o-, m- and p-chloroaniline, N-methylaniline, N-ethylaniline, 3- or 4-acetylaminoaniline, 2,5-dimethoxyaniline, o-, m- and p-anisidine, o-, m- and p-phenetidine, 1-naphthylamine, 2-naphthylamine, 2-amino-1-hydroxynaphthalene, 1-amino-4-hydroxynaphthalene, 1-amino-8-hydroxynaphthalene, 1-amino-2-hydroxynaphthalene, 1-amino-7-hydroxynaphthalene, orthanilic acid, metanilic acid, sulfanilic acid, aniline-2,4-disulfonic acid, aniline-2,5-disulfonic acid, anthranilic acid, m- and p-aminobenzoic acid, 2-aminotoluene-4-sulfonic acid, 2-aminotoluene-5-sulfonic acid, p-aminosalicylic acid, 1-amino-4-carboxybenzene-3-sulfonic acid, 1-amino-2-carboxybenzene-5-sulfonic acid, 1-amino-5-carboxybenzene-2-sulfonic acid, 1-naphthylamine-2-, -3-, -4-, -5-, -6-, -7- and -8-sulfonic acid, 2-naphthylamine-1-, -3-, -4-, -5-, -6-, -7- and -8-sulfonic acid, 2-naphthylamine-2,4-, -2,5-, -27,-, -2,8-, -3,5-, -3,6-, 3,7-, -3,8-, -4,6-, -4,7-, -4,8- and -5,8-disulfonic acid, 2-naphthylamine-1,5-, -1,6-, -1,7-, -3,6-, -3,7-, -4,7-, -4,8-, -5,7- and -6,8-disulfonic acid, 1-naphthylamine-2,4,6-, -2,4,7-, -2,5,7-, -3,5,7-, -3,6,8- and -4,6,8-trisulfonic acid, 2-naphthylamino-1,3,7-, -1,5,7-, -3,5,7-, -3,6,7-, -3,6,8- and -4,6,8-trisulfonic acid, 2-, 3- and 4-aminopyridine, 2-aminobenzthiazole, 5-, 6- and 8-aminoquinoline, 2-aminopyrimidine, morpholino, piperidine, piperazine, water, methanol, ethanol, propanol, isopropanol, n-butanol, isobutanol, sec-butanol, tert-butanol, hexanol, cyclohexanol, β-methoxyethanol, β-ethoxyethanol, γ-methoxypropanol, γ-ethoxypropanol, β-ethoxy-β-ethoxyethanol, glycolic acid, phenol, o-, m- and p-chlorophenol, o-, m- and p-nitrophenol, o-, m- and p-hydroxybenzoic acid, o-, m- and p-phenolsulfonic acid, phenol-2,4-disulfonic acid, α-naphthol, β-naphthol, 1-hydroxynaphthalene-8-sulfonic acid, 2-hydroxynaphthalene-1-sulfonic acid, 1-hydroxynaphthalene-5-sulfonic acid, 1-hydroxynaphthalene-4-sulfonic acid, 1-hydroxynaphthalene-6-, or -7-sulfonic acid, 2-hydroxynaphthalene-6-, 7- or -8-sulfonic acid, 2hydroxynaphthalene-4-sulfonic acid, 2-hydroxynaphthalene-4,8- or -6,8-disulfonic acid, 1-hydroxynaphthalene-4,8-disulfonic acid, 2-hydroxynaphthalene-3,6-disulfonic acid, methanethiol, ethanethiol, propanethiol, isopropanethiol, n-butanethiol, thioglycollic acid, thiourea, thiophenol, α-thionaphthol, β-thionaphthol.

The introduction of the substituent in the 2-position of the triazine radical can also be performed after diazotisation and coupling. Accordingly, one of the above amino, hydroxy or mercapto compounds can be condensed subsequently with a dihalo-s-triazine radical which is already attached to the azo dye.

Examples of useful aminofluorotriazines are: 2-amino-4,6-difluoro-s-triazine, 2-phenylamino-4,6-difluoro-s-triazine, 2-N-methyl-N-phenylamino-4,6-difluoro-s-triazine, 2-(methylphenylamino)-4,6-difluoro-s-triazine, 2-(chlorophenylamino)-4,6-difluoro-s-triazine, 2-(sulfophenylamino)-4,6-difluoro-s-triazine, 2-N-methyl-N-(methylphenylamino)-4,6-difluoro-s-triazine, 2-N-methyl-N-(chlorophenylamino)-4,6-difluoro-s-triazine, 2-N-methyl-N-(sulfophenylamino)-4,6-difluoro-s-triazine and 2-(chloroethylsulfonylethylamino)-4,6-difluoro-s-triazine.

Numerous examples of coupling components of formula (4) which, besides these already mentioned, can be used in the process of the present invention are known from the literature, e.g.: dimethylaniline, diethylaniline, 3-methyldimethylaniline, 3-methyldiethylaniline, 3-acetylamino- or 3-methoxycarbonylamino- or 3-ureidodimethylaniline, 3-methyl-6-methoxydiethylaniline, 2,5-dimethoxydiethylaniline, N-ethyl-N-benzylaniline, N-ethyl-N-(β-cyanoethyl)aniline, N-ethyl-N-(β-hydroxyethyl)aniline, N-ethyl-N-(β-acetoxyethyl)aniline, N,N-dibutylaniline, 3-(α,β-dibromopropionylamino)-N,N-dimethyl- or diethylaniline, 3-(α-chloroacetylamino)- or 3-(α-bromoacryloylamino)-N,N-dimethylaniline, 1-hydroxy-7-amino-3-sulfonaphthalene, 1-hydroxy-7-methylamino- or -7-phenylamino-3-sulfonaphthalene, 1-hydroxy-7-(α,β-dibromopropionylamino)- or 7-(α-chloroacetylamino)-3-sulfonaphthalene, 1-hydroxy-8-amino-3,6- or -3,5-disulfonaphthalene, 1-hydroxy-8-benzoylamino-3,6- or -3,5-disulfonaphthalene, 1-hydroxy-8-ureido-3,6- or -3,5-disulfonaphthalene, 1-hydroxy-8-acetylamino-3,6- or -3,5-disulfonaphthalene, 1-hydroxy-8-(3'-α,β-dibromopropionylaminobenzoylamino)-3,6- or -3,5-disulfonaphthalene, 1-(2',3'- or 4'-sulfophenyl)-3-methylpyrazol-5-one, 1-(2'-chloro-4'- or 5'-sulfophenyl)-3-methylpyrazol-5-one, 1-(2'-methyl-4'-sulfophenyl)-3-methylpyrazol-5-one, 1-[4',8'-disulfonaphthyl-(2)]-3-methylpyrazol-5-one, 1-[5',7'-disulfonaphthyl-(2)]-3-methylpyrazol-5-one, 1-(2'-chloro-5'-sulfophenyl)-3-methyl-5-aminopyrazole, 1-(2'-chloro-4'-sulfophenyl)-3-methyl-5-aminopyrazole, 1-(3'- or 4'-sulfophenyl)-3-methyl-5-aminopyrazole, 1-ethyl-3-cyano-4-methyl-6-hydroxypyrid-2-one, 1-ethyl-4-methyl-6-hydroxypyrid-2-one, 2-methylindole, 2-phenylindole.

The invention also relates to a process for the preparation of compounds of formula (3), which process comprises reacting a compound of formula (2) in an aqueous medium containing 5 to 25% by weight of an alkali metal halide or alkali metal sulfate, based on the weight of the medium, with a compound which introduces the radical X to give the product of formula (3).

Starting materials, process conditions and preferred procedures correspond to the above-described reaction step for the acylation of a phenylenediamine. The compounds of formula (3) are suitable e.g. as diazo components for the preparation of azo compounds.

The azo compounds of formula (1) which can be obtained by the process of this invention are suitable as dyes for dyeing or printing textile fibre materials, in particular polyhydroxylated materials of a fibrous structure such as cellulosic materials, e.g. regenerated cellulose, linen and, especially, cotton. The azo compounds of formula (1) are suitable in particular for dyeing or printing nitrogen-containing textile materials such as silk or, especially, wool and also superpolyamide or superpolyurethane fibres from a weakly alkaline, neutral or acid bath, e.g. an acetate bath.

Compared with the known processes for the preparation of azo dyes of formula (1), the process of this invention has the following advantages, in addition to those mentioned above. Owing to the selective condensation of the phenylenediamine compounds with the acylating agent even in heterogeneous phase, the reaction can be carried out in a more concentrated medium than has so far been possible, which results in a saving of solvent and energy and a reduction in the amount of waste water. Furthermore, with the process of this invention there is less waste water pollution. Owing to the greater purity of the azo compounds obtained by the process of this invention compared with the same azo dyes prepared in conventional manner, in some cases an improvement of the fastness properties of the dyeings obtained can be achieved.

The invention is illustrated by the following Examples. Parts and percentages are by weight. The ratio of parts by weight to parts by volume is the same as that of grams to cubic centimeters.

EXAMPLE 1

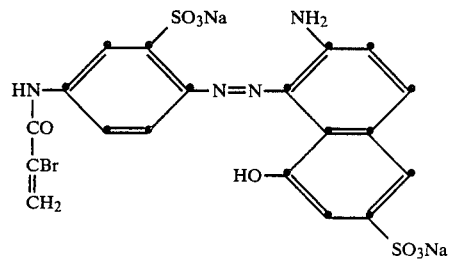

53 parts of 1,4-phenylenediamine-2-sulfonic acid are stirred in 80 parts of water, heated to 50° C. and dissolved at pH 8 by adding aqueous sodium hydroxide solution. The volume is made up to 250 parts with water. About 150 parts of ice are then added. Subsequently, with stirring, 45 parts of sodium chloride followed by 15 parts of sodium acetate and 20 parts of sodium bicarbonate are added at 0° to 3° C. to the resultant solution. 67 parts of 2,3-dibromopropionyl chloride are then added in portions. A temperature in the range from 5° to 10° C. is maintained by the addition of ice. The volume is then made up to 800 parts with water and, with efficient stirring and at about 30° C. 60 parts of 32% hydrochloric acid are added. Diazotisation is effected, under adiabatic conditions, with 62.5 parts of 4N sodium nitrite solution. Any excess nitrite present can be destroyed with sulfamic acid.

66 parts of 2-amino-8-hydroxynaphthalene-6-sulfonic acid are dissolved in 100 parts of water, with the simultaneous addition of 27.5 parts of 30% sodium hydroxide solution. The volume is made up to 350 parts with water. This solution is then added to the above prepared diazo suspension, and the pH is adjusted to 3.8 by adding 30% sodium hydroxide solution. In order to complete the coupling reaction, 15 parts of sodium acetate are then added. When the coupling reaction is complete, the dye solution, is adjusted to pH 11.5 to 12 by adding 50 parts of 30% sodium hydroxide solution, the temperature being maintained in the range from 25° to 30° C. The dye solution is stirred for 15 minutes at pH 11.5 to 12 and then neutralised to pH 6 by the addition of 32% hydrochloric acid. The suspension is subsequently filtered, and the filtrate is dried in vacuo at 70° to 80° C., affording a bluish red powder which dissolves in water and dyes wool from an acetate bath in very wetfast, bluish red shades. The yield in all stages is 90%.

EXAMPLE 2

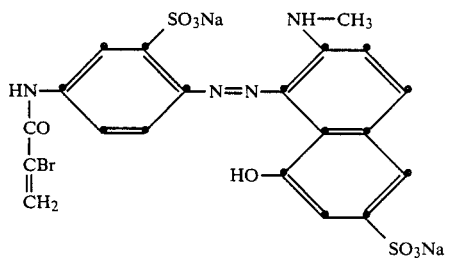

53 parts of 1,4-phenylenediamine-2-sulfonic acid are stirred in 80 parts of water, heated to 50° C. and dissolved at pH 8 by adding aqueous sodium hydroxide solution. The volume is made up to 250 parts with water. About 150 parts of ice are then added. Subsequently, with stirring, 45 parts of sodium chloride followed by 15 parts of sodium acetate and 20 parts of sodium bicarbonate are added at 0° to 3° C. to the resultant solution. 67 parts of 2,3-dibromopropionyl chloride are then added in portions. A temperature in the range from 5° to 10° is maintained by the addition of ice. The volume is then made up to 800 parts with water and, with efficient stirring and at about 30° C., 60 parts of 32% hydrochloric acid are added. Diazotisation is effected, under adiabatic conditions, with 62.5 parts of 4N sodium nitrate solution. Any excess nitrite present can be destroyed with sulfamic acid.

70 parts of 2-N-methylamino-8-hydroxynaphthalene-6-sulfonic acid are dissolved in 100 parts of water, with the simultaneous addition of 27.5 parts of 30% sodium hydroxide solution. The volume is made up to 350 parts with water. This solution is then added to the above prepared diazo suspension, and the pH is adjusted to 3.8 by adding 30% sodium hydroxide solution. In order to complete the coupling reaction, 15 parts of sodium acetate are then added. When the coupling reaction is complete, the dye solution is adjusted to pH 11.5 to 12 by adding 50 parts of 30% sodium hydroxide solution, the temperature being maintained in the range from 25° to 30° C. The dye solution is stirred for 15 minutes at pH 11.5 to 12 and then neutralised to pH 6 by the addition of 32% hydrochloric acid. The suspension is subsequently filtered, and the filtrate is dried in vacuo at 70° to 80° C., affording a bluish red powder which dissolves in water and dyes wool from an acetate bath in very wetfast, reddish blue shades. The yield in all stages is 90%.

EXAMPLE 3

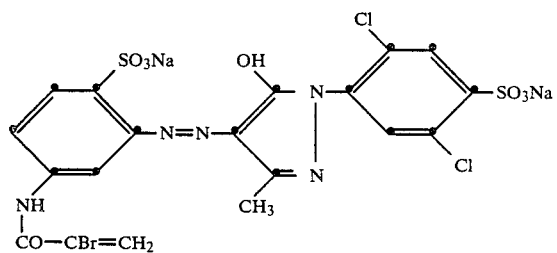

53 parts of 1,3-phenylenediamine-4-sulfonic acid are stirred in 80 parts of water, heated to 60° C. and dissolved at pH 7.5 by adding aqueous sodium hydroxide solution. The volume is then made up to 230 parts with water. Ice is then added. Subsequently, with stirring, 25 parts of sodium chloride are added at 0° to 3° C. to the resultant solution. 70 parts of 2,3-dibromopropionyl chloride are then added in portions. A temperature in the range from 0° to 10° C. is maintained by the addition of ice and the pH is kept constant at 5 by running in sodium hydroxide solution. The volume is then made up to 700 parts with water and, with efficient stirring and at about 30° C., 60 parts of 32% hydrochloric acid are added. Diazotisation is effected, under adiabatic conditions, with 64 parts of 4N sodium nitrite solution. Any excess nitrite present can be destroyed with sulfamic acid.

85.6 parts of (2,5-dichloro-4-sulfo)phenyl-3-methyl-pyrazol-5-one are dissolved in 158 parts of water, with the simultaneous addition of 28 parts of 30% sodium hydroxide solution. The volume is made up to 400 parts with water. This solution is then added to the above prepared diazo suspension, and the pH is adjusted to 5 by adding 30% sodium hydroxide solution. When the coupling reaction is complete, the dye solution is heated to 70° C. and adjusted to pH 6 to 7 by adding 13 parts of 30% sodium hydroxide solution, the temperature being maintained at 70° C. The dye solution is stirred for 20 minutes at pH 6 to 7 and then 35 parts of sodium chloride are added. The suspension is subsequently filtered, and the filtrate is dried in vacuo at 70° to 80° C., affording a yellow powder which dissolves in water and dyes wool from an acetate bath in very wetfast yellow shades. The yield in all stages is 85%.

EXAMPLE 4

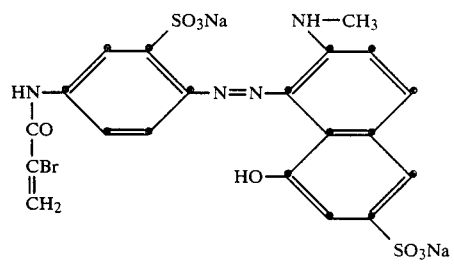

53 parts of 1,4-phenylenediamine-2-sulfonic acid are stirred in 80 parts of water, heated to 50° C. and dissolved at pH 8 by adding aqueous sodium hydroxide solution. The volume is made up to 400 parts. About 180 parts of ice are then added. Subsequently, with stirring, 47 parts of sodium chloride followed by 15 parts of sodium acetate and 20 parts of sodium bicarbonate are added at 0° to 3° C. to the resultant solution. 67 parts of 2,3-dibromopropionyl chloride are then added in portions. A temperature in the range from 5° to 10° C. is maintained by the addition of ice. The volume is then made up to 800 parts with water and, with efficient stirring and at about 30° C. 60 parts of 32% hydrochloric acid are added. Diazotisation is effected, under adiabatic conditions, with 62.5 parts of 4N sodium nitrite solution. Any excess nitrite prsent can be destroyed with sulfamic acid. 70 parts of 2-N-methylamino-8-hydroxynaphthalene-6-sulfonic acid are dissolved in 100 parts of water, with the simultaneous addition of 27.5 parts of 30% sodium hydroxide solution. The volume is made up to 300 parts with water. This solution is added to the above prepared diazo suspension, and the pH is adjusted to 3.8 by adding 30% sodium hydroxide solution. In order to complete the coupling reaction, 15 parts of sodium acetate are then added. When the coupling reaction is complete, the dye solution is adjusted to pH 11.5 to 12 by adding 50 parts of 30% sodium hydroxide solution, the temperature being maintained in the range from 25° to 30° C. The dye solution is stirred for 15 minutes at pH 11.5 to 12 and then neutralised to pH 6 by the addition of 32% hydrochloric acid. The suspension is subsequently filtered, and the filtrate is dried in vacuo at 70° to 80° C., affording a bluish red powder which dissolves in water and dyes wool from an acetate bath in very wetfast, bluish red shades. The yield in all stages is 90%.

By repeating the procedure as indicated in Examples 1 to 4 but using as phenylenediamine 1,3-phenylenediamine-4-sulfonic acid, as acylating agent the acylating agent indicated in column 1 of the Table, in equimolar amount, and as coupling component the coupling component indicated in column 2 of the Table, in equimolar amount, then purer dyes are also obtained than by known methods. The shade of the resultant dyeings on wool is indicated in column 3 of the Table.

TABLE

| Example | Acylating agent | Coupling component | Shade |
|---|---|---|---|
| 5 | 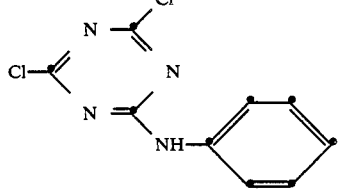 | 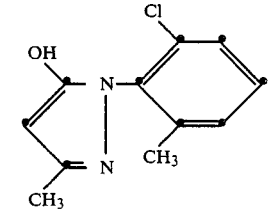 | yellow |
| 6 | Cl—CO—CHCl—CH$_2$Cl | 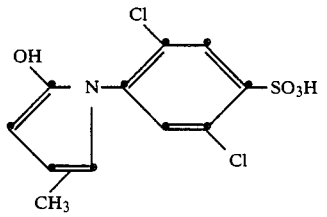 | yellow |
| 7 | Cl—CO—CHCl—CH$_2$Cl | 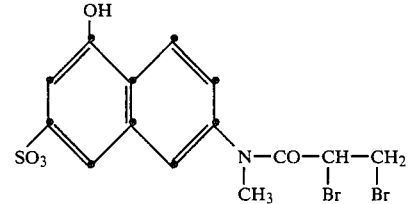 | orange |
| 8 | Cl—CO—CCl=CH$_2$ | 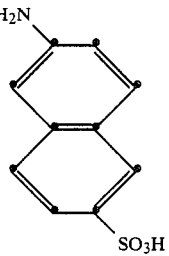 | orange |
| 9 | Cl—CO—CHBr—CH$_2$Br | 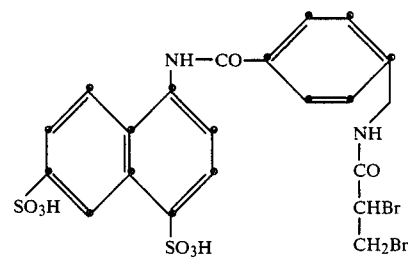 | red |
| 10 | Cl—CO—CHBr—CH$_2$Br | 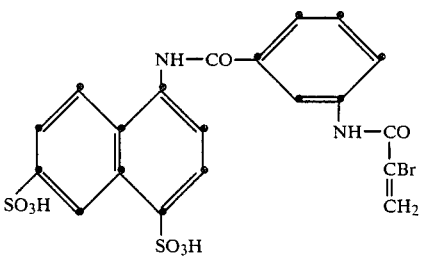 | red |

TABLE -continued

| Example | Acylating agent | Coupling component | Shade |
|---|---|---|---|
| 11 | Cl—CO—CHBr—CH₂Br | 8-hydroxy-6-sulfo-2-(2-bromoacryloylamino)naphthalene | red |
| 12 | Cl—CO—CHBr—CH₂Br | 8-hydroxy-8-acetamido-naphthalene-3,6-disulfonic acid derivative | red |
| 13 | triazine with Cl, Cl, and O—CH(CH₃)₂ substituents | 3-methyl-1-(2-chloro-6-methylphenyl)-5-hydroxypyrazole | yellow |
| 14 | fluoro-chloro-fluoro triazine derivative | 8-hydroxy-6-sulfo-2-aminonaphthalene | bluish red |
| 15 | fluoro-OCH₃-fluoro triazine derivative | 8-hydroxy-6-sulfo-2-aminonaphthalene | bluish red |

EXAMPLE 16

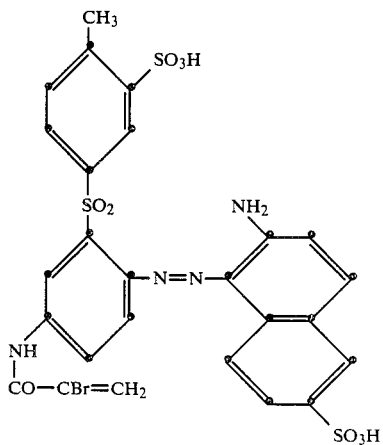

37.6 parts of 2,5-diamino-4'-methyl-1,1'-diphenylsulfone-3'-sulfonic acid are dissolved in 400 parts of water at 40° C. and at pH 7.5 by adding 11.5 parts of 30% sodium hydroxide solution, a clear solution being formed. 25 parts of sodium chloride and 13 parts of sodium bicarbonate are added, the resultant solution is cooled to 0° to 5° C. and, with intensive stirring. 30 parts of α,β-dibromopropionyl chloride are run in. When acylation is complete, the pH is about 6.5. The acylation suspension is made up to 600 parts with ice and water, and 120 parts of α-naphthalenesulfonic acid are then added. Diazotisation is effected at 5° to 10° C. with 25 parts of 4N sodium nitrite solution. Any excess nitrite is destroyed with sulfamic acid. 40 parts of sodium acetate are added.

A suspension consisting of 23.5 parts of 2-aminonaphthalene-6-sulfonic acid in 1000 parts of water of 40° C., which suspension has been adjusted to pH 7 to 7.5 by adding 10.5 parts of 10N sodium hydroxide solution and then made up to a volume of 150 parts with ice, is stirred into the diazo suspension. The pH of the coupling mass is adjusted to 7 by adding about 35 parts of 10N sodium hydroxide solution. The pH is then adjusted to 11.5 to 12 by adding 12 parts of 10N sodium hydroxide solution. After 15 minutes, the pH is adjusted to 8 by adding 2 parts of 10N hydrochloric acid, the precipitated dye is isolated, washed with 3% brine and dried in vacuo at 80° C., affording 70 parts of a brownish red powder which, when dissolved in water, dyes wool from an acetate bath in very wetfast, yellowish red shades.

What is claimed is:

1. A process for the preparation of an azo compound of the formula

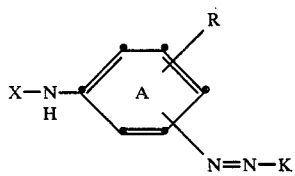

wherein K is the radical of a coupling component, R is a water-solubilizing group and X is a fibre-reactive radical, and the benzene ring A is unsubstituted or further substituted, which process comprises reacting a compound of the formula

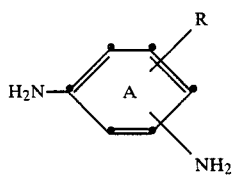

in an aqueous medium containing 5 to 25% by weight of an alkali metal halide or alkali metal sulfate, based on the weight of the medium, with an acylating agent XA' wherein X is as previously defined and A' is a halide or an anhydride of an organic acid or an easily replaceable atom or group on a heterocyclic compound to give a compound of formula

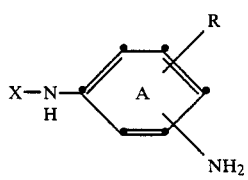

diazotising said compound direct without isolation or purification and coupling the diazotisation product with a coupling component of the formula

 H—K  (4)

in which formulas (2), (3) and (4) A, R, X and K are as defined for formula (1).

2. A process according to claim 1, wherein the weight ratio of water to the compound of formula (2) is in the range from 3:1 to 20:1.

3. A process according to claim 1, which comprises the use of 8 to 13% by weight of an alkali metal halide or alkali metal sulfate.

4. A process according to claim 3, which comprises the use of sodium chloride.

5. A process according to claim 1, wherein X is an acyl group, which comprises carrying out an acylation in the presence of further additional salts.

6. A process according to claim 5, which comprises the use of a mixture of an alkali metal carbonate or alkali metal bicarbonate, an alkali metal acetate and an alkali metal halide or alkali metal sulfate.

7. A process according to claim 1, wherein the reaction of a compound of formula (2) with an acylating agent XA' is carried out in the temperature range from 0° to 20° C. and at a pH in the range from 3 to 9.

8. A process according to claim 1, wherein, in the compound of formula (2), R is a sulfophenylsulfone or a sulfonic acid group.

9. A process according to claim 8, wherein the compound of formula (2) is 2,5-diamino-4'-methyl-1,1'-diphenylsulfone-3'-sulfonic acid or 1,3-phenylenediaminesulfonic acid or 1,4-phenylenediamine-2-sulfonic acid.

10. A process according to claim 1, wherein XA' is selected from is α,β-dibromopropionyl chloride, α,β-dichloropropionyl chloride, α-chloroacryloyl chloride, chloroacetyl chloride or chloroacetic anhydride.

11. A process according to claim 1, wherein the coupling component of formula (4) is a benzene, naphthalene or heterocylic radical.

12. A process according to claim 1 for the preparation of the azo compound of the formula

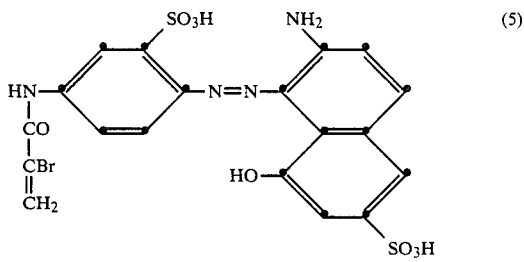

which process comprises reacting 1,4-phenylenediamine-2-sulfonic acid with α,β-dibromopropionyl chloride, diazotising the resultant compound direct without isolation, coupling the diazotisation product with 2-amino-8-hydroxynaphthalene-6-sulfonic acid and subsequently reacting the coupling product with a dehydrobrominating agent.

13. A process according to claim 1 for the preparation of the azo compound of the formula

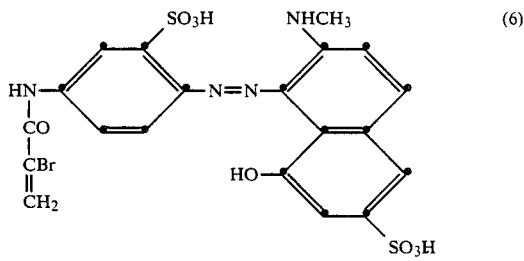

which process comprises reacting 1,4-phenylenediamine-2-sulfonic acid with α,β-dibromopropionyl chloride, diazotising the resultant compound direct without isolation, coupling the diazotisation product with 2-N-methylamino-8-hydroxynaphthalene-6-sulfonic acid and subsequently reacting the coupling product with a dehydrobrominating agent.

14. A process according to claim 1 for the preparation of the azo dye of the formula

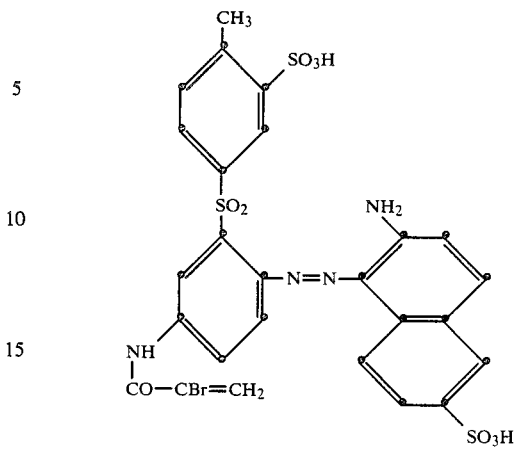

which process comprises reacting 2,5-diamino-4'-methyl-1,1'-diphenylsulfone-3'-sulfonic acid with α,β-dibromopropionyl chloride, diazotising the resultant compound direct without isolation or purification, coupling the diazotisation product with 2-aminonaphthalene-6-sulfonic acid and subsequently reacting the coupling product with a dehydrobrominating agent.

15. A process according to claim 1, wherein the weight ratio of water to the compound of formula (2) is in the range from 4:1 to 8:1.

16. A process according to claim 5, wherein a mixture of salts acts as a buffer.

* * * * *